(12) United States Patent
Wang (10) Patent No.: US 12,223,647 B2
(45) Date of Patent: Feb. 11, 2025

(54) METHOD FOR IDENTIFYING BODY CONSTITUTION IN TRADITIONAL CHINESE MEDICINE, AND COMPUTING AND PROCESSING DEVICE AND NON-TRANSITORY COMPUTER-READABLE MEDIUM THEREOF

(71) Applicant: BOE TECHNOLOGY GROUP CO., LTD., Beijing (CN)

(72) Inventor: Sifan Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 17/772,742

(22) PCT Filed: Jul. 26, 2021

(86) PCT No.: PCT/CN2021/108470
§ 371 (c)(1),
(2) Date: Apr. 28, 2022

(87) PCT Pub. No.: WO2023/004546
PCT Pub. Date: Feb. 2, 2023

(65) Prior Publication Data
US 2024/0169518 A1 May 23, 2024

(51) Int. Cl.
*G06T 7/00* (2017.01)
(52) U.S. Cl.
CPC .. *G06T 7/0012* (2013.01); *G06T 2207/10048* (2013.01); *G06T 2207/20081* (2013.01); *G06T 2207/30004* (2013.01)

(58) Field of Classification Search
CPC ........ G06T 7/0012; G06T 2207/10048; G06T 2207/20081; G06T 2207/30004
See application file for complete search history.

(56) References Cited

U.S. PATENT DOCUMENTS

| 12,014,549 B2 * | 6/2024 | Pan | G06T 7/337 |
| 2009/0326381 A1 * | 12/2009 | Yuan | A61B 5/015 |
| | | | 600/473 |

(Continued)

FOREIGN PATENT DOCUMENTS

| CN | 101015448 A | 8/2007 |
| CN | 107133967 A | 9/2017 |

(Continued)

*Primary Examiner* — Ming Y Hon
(74) *Attorney, Agent, or Firm* — WHDA, LLP (57) ABSTRACT

The present disclosure provides a method and an apparatus for identifying a body constitution, an electronic device, a storage medium and a program, which relates to the technical field of computers. The method includes: acquiring an infrared human-body image of a target user; inputting the infrared human-body image into an infrared critical-point identifying model, to obtain a Traditional-Chinese-Medicine human-body critical point in the infrared human-body image; according to a temperature-distribution profile in the infrared human-body image, determining a temperature type of the Traditional-Chinese-Medicine human-body critical point in the infrared human-body image; and according to the temperature type, identifying a Traditional-Chinese-Medicine body constitution of the target user.

16 Claims, 7 Drawing Sheets

(56) References Cited

U.S. PATENT DOCUMENTS

| | | | |
|---|---|---|---|
| 2019/0320909 A1* | 10/2019 | Lo | G06T 7/0016 |
| 2020/0121556 A1* | 4/2020 | Tian | A61H 39/02 |
| 2021/0213048 A1* | 7/2021 | Lo | A61B 5/015 |
| 2022/0224860 A1* | 7/2022 | Xu | H04N 21/4788 |
| 2022/0301278 A1* | 9/2022 | Lu | G06V 10/94 |
| 2022/0346885 A1* | 11/2022 | Kunio | A61B 6/5247 |
| 2023/0013508 A1* | 1/2023 | Sharma | G06N 3/09 |
| 2023/0044102 A1* | 2/2023 | Anderson | G06N 20/20 |
| 2023/0170069 A1* | 6/2023 | Groteke | G16H 30/40 |
| | | | 382/128 |
| 2023/0175861 A1* | 6/2023 | G?nther | G06T 7/73 |
| | | | 348/135 |
| 2023/0213388 A1* | 7/2023 | Feng | G06V 10/143 |
| | | | 374/121 |
| 2024/0153133 A1* | 5/2024 | Woo | G06T 7/74 |
| 2024/0161374 A1* | 5/2024 | Torn?us | G06T 13/40 |

FOREIGN PATENT DOCUMENTS

| | | | |
|---|---|---|---|
| CN | 108065915 | * | 5/2018 |
| CN | 108065915 A | | 5/2018 |
| JP | 2019105460 A | | 6/2019 |

* cited by examiner

METHOD FOR IDENTIFYING BODY CONSTITUTION IN TRADITIONAL CHINESE MEDICINE, AND COMPUTING AND PROCESSING DEVICE AND NON-TRANSITORY COMPUTER-READABLE MEDIUM THEREOF

TECHNICAL FIELD

The present disclosure relates to the technical field of computers, and particularly relates to a method and an apparatus for identifying a body constitution in Traditional Chinese Medicine, an electronic device, a storage medium and a program.

BACKGROUND

Infrared imaging is extension of the "looking" in the four ways of diagnosis of the Traditional Chinese Medicine of "looking, listening, questioning and pulse feeling". The infrared-image analysis in the Traditional Chinese Medicine is usually performed by a trained doctor of the Traditional Chinese Medicine, and includes manually processing an infrared human-body image by using color chromatography, analyzing the physical signs of coldness and hotness of body sites by watching the infrared human-body image that has been processed, and determining the classification of the Traditional-Chinese-Medicine body constitutions such as coldness depression and hotness obstruction by comprehensive analysis on the physical signs of the coldness and hotness of several key sites such as hands, feet, head, neck, abdomen and stomach. Doctors of the Traditional Chinese Medicine that have not been trained or have little experience cannot accurately determine the physical signs of patients.

SUMMARY

The present disclosure provides a method and an apparatus for identifying a body constitution in Traditional Chinese Medicine, an electronic device, a storage medium and a program.

Some embodiments of the present disclosure provide a method for identifying a body constitution in Traditional Chinese Medicine, wherein the method includes:
  acquiring an infrared human-body image of a target user;
  inputting the infrared human-body image into an infrared critical-point identifying model, to obtain a Traditional-Chinese-Medicine human-body critical point in the infrared human-body image;
  according to a temperature-distribution profile in the infrared human-body image, determining a temperature type of the Traditional-Chinese-Medicine human-body critical point in the infrared human-body image; and
  according to the temperature type, identifying a Traditional-Chinese-Medicine body constitution of the target user.

Optionally, the infrared critical-point identifying model is obtained by the following steps:
  acquiring a natural-light critical-point identifying model and a sample infrared human-body image;
  marking the Traditional-Chinese-Medicine human-body critical point in the sample infrared human-body image; and
  performing transfer learning of the natural-light critical-point identifying model by using the sample infrared human-body image that has been marked, to obtain the infrared critical-point identifying model.

Optionally, the step of performing transfer learning of the natural-light critical-point identifying model by using the sample infrared human-body image that has been marked, to obtain the infrared critical-point identifying model includes:
  based on the Traditional-Chinese-Medicine human-body critical point, adjusting fully-connected-layer nodes of the natural-light critical-point identifying model; and
  while a model parameter of a feature-extraction layer is maintained unchanged, by using the sample infrared human-body image that has been marked, training the natural-light critical-point identifying model whose nodes have been adjusted, to obtain the infrared critical-point identifying model.

Optionally, original human-body critical points of the natural-light critical-point identifying model include the Traditional-Chinese-Medicine human-body critical point, and a quantity of the original human-body critical points is greater than a quantity of the Traditional-Chinese-Medicine human-body critical point; and
  the step of, based on the Traditional-Chinese-Medicine human-body critical point, adjusting the fully-connected-layer nodes of the natural-light critical-point identifying model includes:
  among the fully-connected-layer nodes of the natural-light critical-point identifying model, deleting a fully-connected-layer node whose node label corresponds to a human-body critical point that is not the Traditional-Chinese-Medicine human-body critical point.

Optionally, the step of performing transfer learning of the natural-light critical-point identifying model by using the sample infrared human-body image that has been marked, to obtain the infrared critical-point identifying model includes:
  based on the Traditional-Chinese-Medicine human-body critical point, adjusting fully-connected-layer nodes of the natural-light critical-point identifying model; and
  by using the sample infrared human-body image that has been marked, training the natural-light critical-point identifying model whose nodes have been adjusted, to obtain the infrared critical-point identifying model.

Optionally, a feature-extraction network in the natural-light critical-point identifying model is a lightweight feature-extraction network, wherein a parameter data volume of the lightweight feature-extraction network is less than a parameter data volume of an original feature-extraction network of the natural-light critical-point identifying model.

Optionally, the Traditional-Chinese-Medicine human-body critical point includes at least one of a head critical point, a neck critical point, a shoulder critical point, an elbow critical point, a hand critical point, an abdomen critical point, a crotch critical point, a knee critical point and a foot critical point.

Optionally, the temperature type includes at least one of a high-temperature types and a low-temperature type; and
  the step of, according to the temperature-distribution profile in the infrared human-body image, determining the temperature type of the Traditional-Chinese-Medicine human-body critical point in the infrared human-body image includes:
  determining maximum-temperature-value positions of a first quantity and/or minimum-temperature-value positions of a second quantity in the infrared human-body image; and
  determining the temperature type of the Traditional-Chinese-Medicine human-body critical point that corresponds to an image region where the maximum-temperature-value positions are located as the high-temperature type, and/or determining the temperature type of the Traditional-Chinese-Medicine human-body critical point that corresponds to an image region where the minimum-temperature-value positions are located as the low-temperature type.

Optionally, the step of determining the maximum-temperature-value positions of the first quantity and/or the minimum-temperature-value positions of the second quantity in the infrared human-body image includes:

by using a maximum-value filter, acquiring image positions where maximum temperature values of the first quantity are located in the infrared human-body image as the maximum-temperature-value positions;

by using a mean value between a maximum temperature value and a minimum temperature value in the infrared human-body image as an inversion plane, inverting temperature values in the infrared human-body image; and by using the maximum-value filter, acquiring positions where maximum temperature values of the second quantity are located in the infrared human-body image that has been inverted as the minimum-temperature-value positions.

Optionally, the step of, according to the temperature type, identifying the Traditional-Chinese-Medicine body constitution of the target user includes:

in a Traditional-Chinese-Medicine-body-constitution mapping relation, inquiring Traditional-Chinese-Medicine body constitutions that match with temperature types of the Traditional-Chinese-Medicine human-body critical points.

Optionally, the step of acquiring the infrared human-body image of the target user includes:

acquiring an initial infrared image obtained by photographing by the user by using an infrared camera;

performing global threshold searching to the initial infrared image by using a human-body-temperature-range threshold, to set the values of the pixel points in the initial infrared image that are within the human-body-temperature-range threshold to be 1, and set the values of the pixel points that are beyond the human-body-temperature-range threshold to be 0, to obtain a binarized initial infrared image; and multiplying the initial infrared image and the binarized initial infrared image, to obtain the infrared human-body image.

Optionally, the step of performing transfer learning of the natural-light critical-point identifying model by using the sample infrared human-body image that has been marked, to obtain the infrared critical-point identifying model includes:

based on the Traditional-Chinese-Medicine human-body critical point, adjusting fully-connected-layer nodes of the natural-light critical-point identifying model; and while some of the predetermined model parameters of a feature-extraction layer are maintained unchanged, by using the sample infrared human-body image that has been marked, training the natural-light critical-point identifying model whose nodes have been adjusted, to obtain the infrared critical-point identifying model.

Optionally, the Traditional-Chinese-Medicine human-body critical point includes at least one of a head critical point, a neck critical point, a shoulder critical point, an elbow critical point, a hand critical point, an abdomen critical point, a crotch critical point, a knee critical point and a foot critical point.

Some embodiments of the present disclosure provide an apparatus for identifying a body constitution in Traditional Chinese Medicine, wherein the apparatus includes:

a receiving module configured for acquiring an infrared human-body image of a target user;

a model predicting module configured for inputting the infrared human-body image into an infrared critical-point identifying model, to obtain a Traditional-Chinese-Medicine human-body critical point in the infrared human-body image; and an identifying module configured for, according to a temperature-distribution profile in the infrared human-body image, determining a temperature type of the Traditional-Chinese-Medicine human-body critical point in the infrared human-body image; and according to the temperature type, identifying a Traditional-Chinese-Medicine body constitution of the target user.

Optionally, the apparatus further includes: a training module configured for:

acquiring a natural-light critical-point identifying model and a sample infrared human-body image;

marking the Traditional-Chinese-Medicine human-body critical point in the sample infrared human-body image; and performing transfer learning of the natural-light critical-point identifying model by using the sample infrared human-body image that has been marked, to obtain the infrared critical-point identifying model.

Optionally, the training module is further configured for:

based on the Traditional-Chinese-Medicine human-body critical point, adjusting fully-connected-layer nodes of the natural-light critical-point identifying model; and while a model parameter of a feature-extraction layer is maintained unchanged, by using the sample infrared human-body image that has been marked, training the natural-light critical-point identifying model whose nodes have been adjusted, to obtain the infrared critical-point identifying model.

Optionally, original human-body critical points of the natural-light critical-point identifying model include the Traditional-Chinese-Medicine human-body critical point, and a quantity of the original human-body critical points is greater than a quantity of the Traditional-Chinese-Medicine human-body critical point; and optionally, the training module is further configured for:

among the fully-connected-layer nodes of the natural-light critical-point identifying model, deleting a fully-connected-layer node whose node label corresponds to a human-body critical point that is not the Traditional-Chinese-Medicine human-body critical point.

Optionally, a feature-extraction network in the natural-light critical-point identifying model is a lightweight feature-extraction network, wherein a parameter data volume of the lightweight feature-extraction network is less than a parameter data volume of an original feature-extraction network of the natural-light critical-point identifying model.

Optionally, the temperature type includes at least one of a high-temperature type and a low-temperature type; and the identifying module is further configured for:

determining maximum-temperature-value positions of a first quantity and/or minimum-temperature-value positions of a second quantity in the infrared human-body image; and determining the temperature type of the Traditional-Chinese-Medicine human-body critical point that corresponds to an image region where the maximum-temperature-value positions are located as the high-temperature type, and/or determining the temperature type of the Traditional-Chinese-Medicine human-body critical point that corresponds to an image region where the minimum-temperature-value positions are located as the low-temperature type.

Optionally, the identifying module is further configured for:
- by using a maximum-value filter, acquiring image positions where maximum temperature values of the first quantity are located in the infrared human-body image as the maximum-temperature-value positions;
- by using a mean value between a maximum temperature value and a minimum temperature value in the infrared human-body image as an inversion plane, inverting temperature values in the infrared human-body image; and
- by using the maximum-value filter, acquiring positions where maximum temperature values of the second quantity are located in the infrared human-body image that has been inverted as the minimum-temperature-value positions.

Optionally, the identifying module is further configured for:
- in a Traditional-Chinese-Medicine-body-constitution mapping relation, inquiring Traditional-Chinese-Medicine body constitutions that match with temperature types of the Traditional-Chinese-Medicine human-body critical points.

Optionally, the receiving module is further configured for:
- acquiring an initial infrared image obtained by photographing by the user by using an infrared camera;
- performing global threshold searching to the initial infrared image by using a human-body-temperature-range threshold, to set the values of the pixel points in the initial infrared image that are within the human-body-temperature-range threshold to be 1, and set the values of the pixel points that are beyond the human-body-temperature-range threshold to be 0, to obtain a binarized initial infrared image; and
- multiplying the initial infrared image and the binarized initial infrared image, to obtain the infrared human-body image.

Optionally, the training module is further configured for:
- based on the Traditional-Chinese-Medicine human-body critical point, adjusting fully-connected-layer nodes of the natural-light critical-point identifying model; and
- while some of the predetermined model parameters of a feature-extraction layer are maintained unchanged, by using the sample infrared human-body image that has been marked, training the natural-light critical-point identifying model whose nodes have been adjusted, to obtain the infrared critical-point identifying model.

Optionally, the Traditional-Chinese-Medicine human-body critical point includes at least one of a head critical point, a neck critical point, a shoulder critical point, an elbow critical point, a hand critical point, an abdomen critical point, a crotch critical point, a knee critical point and a foot critical point.

Some embodiments of the present disclosure provide a computing and processing device, wherein the computing and processing device includes:
- a memory storing a computer-readable code; and
- one or more processors, wherein when the computer-readable code is executed by the one or more processors, the computing and processing device executes the method for identifying a body constitution in Traditional Chinese Medicine stated above.

Some embodiments of the present disclosure provide a computer program, wherein the computer program includes a computer-readable code, and when the computer-readable code is executed in a computing and processing device, the computer-readable code causes the computing and processing device to execute the method for identifying a body constitution in Traditional Chinese Medicine stated above.

Some embodiments of the present disclosure provide a computer-readable medium, wherein the computer-readable medium stores the method for identifying a body constitution in Traditional Chinese Medicine stated above.

The above description is merely a summary of the technical solutions of the present disclosure. In order to more clearly know the elements of the present disclosure to enable the implementation according to the contents of the description, and in order to make the above and other purposes, features and advantages of the present disclosure more apparent and understandable, the particular embodiments of the present disclosure are provided below.

BRIEF DESCRIPTION OF THE DRAWINGS

In order to more clearly illustrate the technical solutions of the embodiments of the present disclosure or the prior art, the figures that are required to describe the embodiments or the prior art will be briefly introduced below. Apparently, the figures that are described below are embodiments of the present disclosure, and a person skilled in the art can obtain other figures according to these figures without paying creative work.

DETAILED DESCRIPTION

In order to make the objects, the technical solutions and the advantages of the embodiments of the present disclosure clearer, the technical solutions of the embodiments of the present disclosure will be clearly and completely described below with reference to the drawings of the embodiments of the present disclosure. Apparently, the described embodiments are merely certain embodiments of the present disclosure, rather than all of the embodiments. All of the other embodiments that a person skilled in the art obtains on the basis of the embodiments of the present disclosure without paying creative work fall within the protection scope of the present disclosure.

Figure 1:
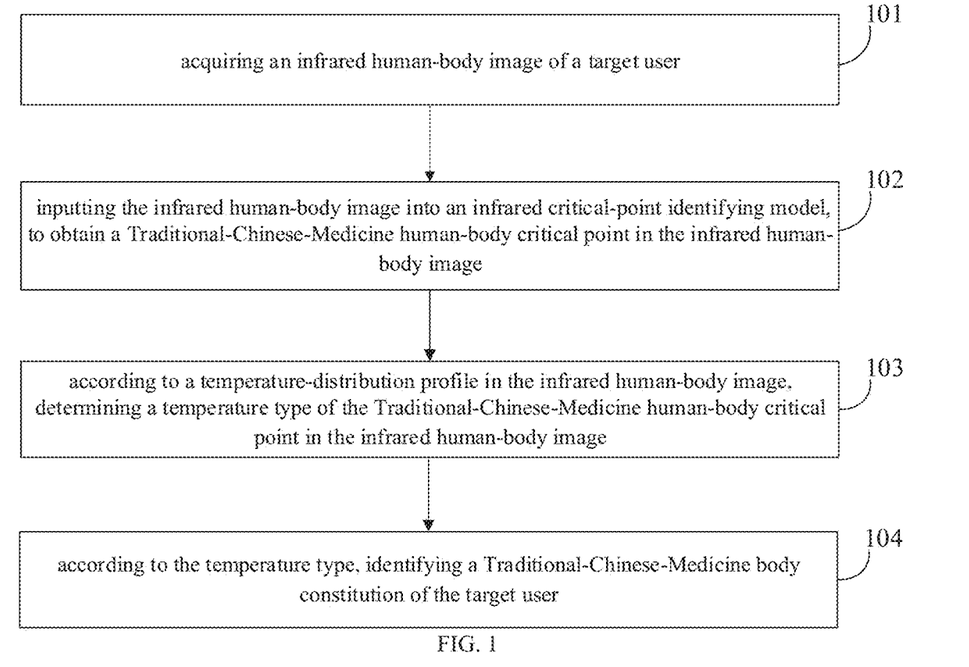
FIG. 1 schematically shows a first schematic flow chart of the method for identifying a body constitution in Traditional Chinese Medicine according to some embodiments of the present disclosure.

FIG. 1 schematically shows a schematic flow chart of the method for identifying a body constitution in Traditional Chinese Medicine according to the present disclosure. The executive body of the method may be any electronic device; for example, the method may be applied to an application program that has the functions such as information displaying, information transmission and data processing, and the method may be executed by a server or a terminal device of the application program. Optionally, the method may be executed by the terminal device. The method includes:

Step 101: acquiring an infrared human-body image of a target user.

In an embodiment of the present disclosure, the target user refers to the user that requires to be identified with respect to the Traditional-Chinese-Medicine body constitution this time. The infrared human-body image refers to an infrared image that is obtained by photographing the target user by using an infrared camera or an image collecting device carrying an infrared camera. Therefore, the values of the pixel points in the infrared human-body image can reflect the profile of the body temperatures of the human-body sites of the user. The photographing of the image may be performed each time the user requires to perform the identification with respect to the Traditional-Chinese-Medicine body constitution. In some embodiments, the infrared human-body image of the target user may also be acquired by acquiring an infrared human-body image that has already been stored in a memory or an infrared human-body image sent by another device, or in another manner, which is not limited herein. For example, an infrared image that is obtained by photographing by using an infrared camera or an image collecting device carrying an infrared camera is stored, for subsequent invoking.

In some embodiments of the present disclosure, the infrared human-body image may be obtained by photographing the target user by using a terminal device carrying an infrared camera, for example, a computer connected to an infrared camera, and the infrared human-body image may also be obtained by photographing the target user by using an infrared camera and subsequently be sent to a terminal device such as a mobile phone, a personal computer or a tablet personal computer of the user, to be used by the terminal device to implement the subsequent steps to identify the Traditional-Chinese-Medicine body constitution.

In some embodiments of the present disclosure, the photographing may be performed at the front face of the human body or at another angle, which is not limited herein.

Step 102: inputting the infrared human-body image into an infrared critical-point identifying model, to obtain a Traditional-Chinese-Medicine human-body critical point in the infrared human-body image.

In an embodiment of the present disclosure, the Traditional-Chinese-Medicine human-body critical point refers to a human-body position that is required to be referred to in the identification with respect to the Traditional-Chinese-Medicine body constitution, and, for example, may include at least one of a head critical point, a neck critical point, a shoulder critical point, an elbow critical point, a hand critical point, an abdomen critical point, a crotch critical point, a knee critical point and a foot critical point. The critical points of some sites may be abandoned, for example the eye critical point and the nose critical point. The critical points that do not have an obvious effect on the identification with respect to the Traditional-Chinese-Medicine body constitution may be abandoned, to reduce the calculation amount. Moreover, the critical points that have an obvious effect on the identification with respect to the Traditional-Chinese-Medicine body constitution, such as the head critical point, may be maintained, to ensure the accuracy of the identification result. It can be understood that the critical points of the other human-body sites may also serve as the Traditional-Chinese-Medicine human-body critical points, which may be particularly determined according to practical demands, and is not limited herein. The infrared critical-point identifying model refers to a machine model for identifying the Traditional-Chinese-Medicine human-body critical points in the body of the user in the infrared human-body image.

In some embodiments of the present disclosure, the terminal device is installed with a client deployed with the application program of the infrared critical-point identifying model, whereby the terminal device, after receiving the human-body infrared image that requires the identification with respect to the Traditional-Chinese-Medicine body constitution, invokes the infrared critical-point identifying model to identify the Traditional-Chinese-Medicine human-body critical points in the infrared human-body image. Certainly, the infrared critical-point identifying model may also be deployed in a server, whereby the client may send the infrared human-body image to the server, the server performs the identification with respect to the Traditional-Chinese-Medicine body constitution, and the result is subsequently returned to the client to be displayed for the user to view.

Step 103: according to a temperature-distribution profile in the infrared human-body image, determining a temperature type of the Traditional-Chinese-Medicine human-body critical point in the infrared human-body image.

In an embodiment of the present disclosure, the temperature type may be used to describe the type of the profile of coldness and hotness of a human body in the academic theory of the Traditional Chinese Medicine. In the theory of the Traditional Chinese Medicine, whether a human-body site is of coldness or hotness is based on the comparison between the temperatures of the sites of a human body, and cannot be measured based on a certain standard temperature threshold. For example, the temperatures of most of the body sites of a certain target user are 36.9°, and the temperature of the feet is 36.5°. Therefore, the feet of the user belong to coldness of a lower temperature. The temperature of the head is 37.1°, and accordingly the head of the user belongs to hotness of a higher temperature. Therefore, in the identification with respect to the Traditional-Chinese-Medicine body constitution of the user, it is required to measure the temperature types of the Traditional-Chinese-Medicine human-body critical points based on the temperature-distribution profile in the infrared human-body image.

In some embodiments of the present disclosure, the temperature types of the image regions where the Traditional-Chinese-Medicine human-body critical points are located may be measured based on the extreme temperature values of the pixel points in the infrared human-body image. For example, the Traditional-Chinese-Medicine human-body critical points in the image region where the maximum value is located are called of hotness, and the Traditional-Chinese-Medicine human-body critical points in the image region where the minimum value is located are called of coldness. Certainly, the temperature types may also be measured based on an overall temperature mean value of the pixel points. For example, the Traditional-Chinese-Medicine human-body critical points whose temperature mean value of the image region where they are located is greater than the overall temperature mean value are called of hotness, and the Traditional-Chinese-Medicine human-body critical points less than the overall temperature mean value are called of coldness. The overall temperature mean value may be a single value, and may also be a value range, which may be particularly configured according to practical demands, and is not limited herein.

Step 104: according to the temperature type, identifying a Traditional-Chinese-Medicine body constitution of the target user.

In some embodiments, the Traditional-Chinese-Medicine body constitution of the user is determined according to the temperature type of the body site where a critical point is located. For example, the temperature type of the critical point of the stomach is of coldness, then it is determined that his Traditional-Chinese-Medicine body constitution is stomach coldness.

In an embodiment of the present disclosure, a knowledge base may be provided by using the mode of determining Traditional-Chinese-Medicine body constitutions in the academic theory of the Traditional Chinese Medicine, thereby, according to the temperature types of the Traditional-Chinese-Medicine human-body critical points, inquiring the knowledge base to acquire the Traditional-Chinese-Medicine body constitution of the target user. For example, if the critical point of the head site is hot, and the critical point of a limb site is of coldness, then it can be determined that the Traditional-Chinese-Medicine body constitution of the target user is a body constitution of yang deficiency. Alternatively, the Traditional-Chinese-Medicine human-body critical points are neither of coldness nor of hotness, then it can be determined that the Traditional-Chinese-Medicine body constitution of the target user is a body constitution of moderation, and so on. That may be particularly configured according to practical demands, and is not limited herein.

The terminal device may display, by using a display screen, the Traditional-Chinese-Medicine body constitution that is identified out, for the user to view. For example, it may also be provided to the user by modes such as voice playing, and the particular form is not limited herein.

In the embodiments of the present disclosure, the temperature types of the sites of the body of the user are identified by using the infrared critical-point identifying model to determine the Traditional-Chinese-Medicine body constitution of the user, which prevents errors in the distinguishing of the temperature types caused by artificial negligence, and improves the accuracy of the identification on the Traditional-Chinese-Medicine body constitution.

Figure 2:
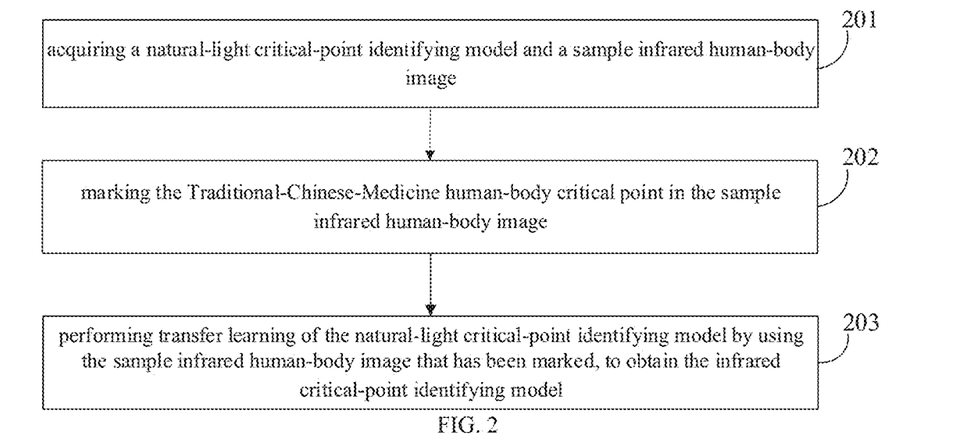
FIG. 2 schematically shows a schematic flow chart of the model training method according to some embodiments of the present disclosure.

Optionally, referring to FIG. 2, the infrared critical-point identifying model is obtained by:

step 201: acquiring a natural-light critical-point identifying model and a sample infrared human-body image.

In an embodiment of the present disclosure, the sample infrared human-body image may be an infrared human-body image that is obtained by photographing a sample user by using an infrared camera and so on. The natural-light critical-point identifying model is an image identifying model that has already been trained, and may identify the human-body critical points in a natural-light image, which may particularly refer to human-body-critical-point identifying models in the related art, and is not discussed herein further.

Step 202: marking the Traditional-Chinese-Medicine human-body critical point in the sample infrared human-body image.

Figure 3:
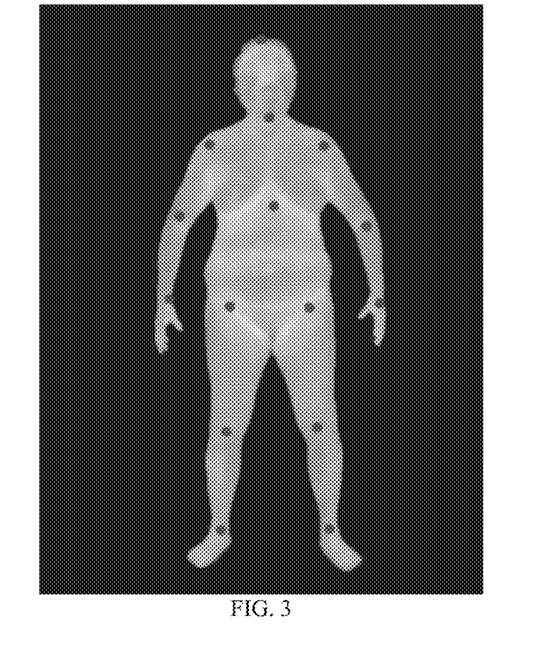
FIG. 3 schematically shows a first schematic effect picture of the sample marking method according to some embodiments of the present disclosure.

In an embodiment of the present disclosure, referring to FIG. 3, the Traditional-Chinese-Medicine human-body critical point may merely select at least one of a head critical point, a neck critical point, a shoulder critical point, an elbow critical point, a hand critical point, an abdomen critical point, a crotch critical point, a knee critical point and a foot critical point. Among them, each of the shoulder critical point, the elbow critical point, the hand critical point, the crotch critical point, the knee critical point and the foot critical point includes a left critical point and a right critical point according to the left-right symmetrical arrangement of a human body. Therefore, totally 15 Traditional-Chinese-Medicine human-body critical points may be provided. Further, the human-body critical points that are not paid attention to in the academic theory of the Traditional Chinese Medicine such as the eye critical point and the nose critical point are abandoned. Because in the related art of natural-light human-body critical points there is a large scale of marking datasets, by directly using the part for natural-light human-body critical points, the disadvantage that the critical-point marking datasets for infrared human-body images in the related art are very rare can be overcome, and it is merely required to screen the human-body critical points in the related art according to the types of the critical points, which reduces the resource required by the sample marking.

Optionally, a feature-extraction network in the natural-light critical-point identifying model is a lightweight feature-extraction network, wherein a parameter data volume of the lightweight feature-extraction network is less than a parameter data volume of an original feature-extraction network of the natural-light critical-point identifying model.

In some embodiments, the original feature-extraction network of the natural-light critical-point identifying model may be replaced by a lightweight feature-extraction network, wherein the parameter data volume of the lightweight feature-extraction network is less than the parameter data volume of the original feature-extraction network.

In some embodiments of the present disclosure, the natural-light critical-point identifying model may be an OpenPose human-body-critical-point detecting model. The model parameters of the feature-extraction network of the original model are approximately 200M, and the data volume and the calculation amount are large. Therefore, in order to reduce the parameter quantity and the calculation amount, Mobilennet (a lightweight feature-extraction network) may be used to replace the original feature-extraction network of the original model, which enables the model parameters to be reduced to 7M, and greatly reduces the calculation amount required by the model training. By providing the natural-light critical-point identifying model of the lightweight feature-extraction network as a pre-training module, and by using the model parameters of the pre-training model as the parameters, the initialization is performed, wherein the initial learning rate is 3e-3. The training continues for 300 epochs (each round of a completed training of the dataset is referred to as one epoch), and the training is reduced by ⅒ every 100 epochs.

Step 203: performing transfer learning of the natural-light critical-point identifying model by using the sample infrared human-body image that has been marked, to obtain the infrared critical-point identifying model.

In an embodiment of the present disclosure, the natural-light critical-point identifying model refers to a machine model for identifying the human-body critical points in a natural-light human-body image. It differs from the infrared critical-point identifying model not only in that the inputs of the models are different, but also in that the natural-light critical-point identifying model is obtained by performing model training based on natural-light human-body images. Therefore, the classifier in the natural-light critical-point identifying model can merely identify the human-body critical points in a natural-light human-body image, and cannot identify the Traditional-Chinese-Medicine human-body critical points in an infrared human-body image. However, thanks to the characteristic of clear boundaries of natural-light human-body images, the feature-extraction layer of the natural-light critical-point identifying model can accurately extract the image features of a human-body image. Therefore, an embodiment of the present disclosure directly uses the model parameters of the feature-extraction layer of the natural-light critical-point identifying model that has already been trained, and re-trains the natural-light critical-point identifying model by using the sample infrared human-body image marked with the Traditional-Chinese-Medicine human-body critical points. By replacing the input of the natural-light critical-point identifying model by the sample infrared human-body image that has been marked, the training target is replaced from the original critical points by the Traditional-Chinese-Medicine human-body critical points to perform transfer learning to the classifier of the natural-light critical-point identifying model, to obtain the infrared critical-point identifying model. The infrared critical-point identifying model can be obtained by transfer learning, and has a good capacity of identification on the image texture, which improves the accuracy of the identification on the Traditional-Chinese-Medicine human-body critical points.

Figure 4:
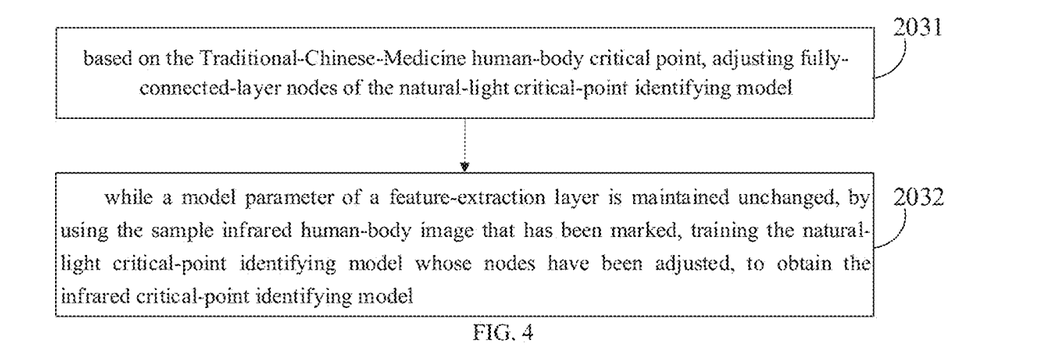
FIG. 4 schematically shows a second schematic flow chart of the model training method according to some embodiments of the present disclosure.

Optionally, referring to FIG. 4, the step 203 may include:

Step 2031: based on the Traditional-Chinese-Medicine human-body critical point, adjusting fully-connected-layer nodes of the natural-light critical-point identifying model.

Step 2032: while a model parameter of a feature-extraction layer is maintained unchanged, by using the sample infrared human-body image that has been marked, training the natural-light critical-point identifying model whose nodes have been adjusted, to obtain the infrared critical-point identifying model.

In some embodiments of the present disclosure, the transfer learning particularly uses the model parameters of the feature-extraction layer of the natural-light critical-point identifying model as the initial training parameters. In some embodiments, the parameters of the feature-extraction layer may be changed, and may also be unchanged, which is determined according to the effect of training. Moreover, the parameters of the other layers are continuously adjusted during the training, such as the fully connected layer, till the training ends. In some embodiments, by not changing the parameters of the feature-extraction layer, a better effect is obtained.

Optionally, the step 2032 may be replaced by: while some of the predetermined model parameters of a feature-extraction layer are maintained unchanged, by using the sample infrared human-body image that has been marked, training the natural-light critical-point identifying model whose nodes have been adjusted, to obtain the infrared critical-point identifying model.

In some embodiments of the present disclosure, in the process of the transfer learning, the parameters of the whole or part of the feature-extraction network may be adjusted, the parameters of the feature-extraction network may be totally changed or partially changed, and the parameters of the other layers are continuously adjusted during the training, which may be particularly configured according to practical demands, and is not limited herein.

Optionally, original human-body critical points of the natural-light critical-point identifying model include the Traditional-Chinese-Medicine human-body critical point, and a quantity of the original human-body critical points is greater than a quantity of the Traditional-Chinese-Medicine human-body critical point; and the step 2031 may include: among the fully-connected-layer nodes of the natural-light critical-point identifying model, deleting a fully-connected-layer node whose node label corresponds to a human-body critical point that is not the Traditional-Chinese-Medicine human-body critical point.

In some embodiments, regarding the identification with respect to the Traditional-Chinese-Medicine body constitution, the quantity of the critical points required to be extracted based on the natural-light image and the quantity of the critical points extracted based on the infrared image are different. Therefore, for the re-training, it is required to adjust the quantity of the critical points, which means that it is required to adjust the node quantity of the fully connected layer of the natural-light critical-point identifying model. Generally, the node quantity of the fully connected layer is adjusted, increased or reduced according to practical demands. For example, because for the natural-light image the eye critical point is important, while for the infrared image the eye critical point is not important, the label of that node is deleted at the fully connected layer, wherein the label contains the coordinate of a critical node and the name of the body site where it is located. By transfer learning by directly using at least some of the model parameters, the infrared critical-point identifying model that can identify the Traditional-Chinese-Medicine human-body critical points in the infrared human-body image is obtained, whereby the model can identify the Traditional-Chinese-Medicine human-body critical points in the infrared human-body image while taking into consideration the capacity of accurate extraction of the image features by the natural-light critical-point identifying model.

Figure 5:
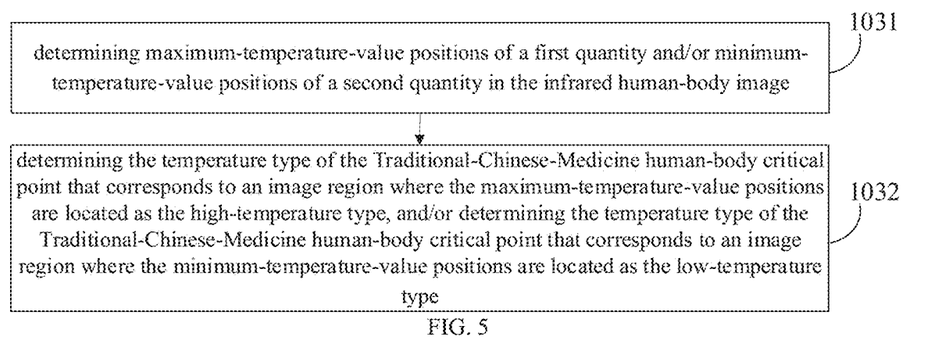
FIG. 5 schematically shows a second schematic flow chart of the method for identifying a body constitution in Traditional Chinese Medicine according to some embodiments of the present disclosure.

Optionally, the temperature type includes at least one of a high-temperature type and a low-temperature type, and, referring to FIG. 5, the step 103 may include:

step 1031: determining maximum-temperature-value positions of a first quantity and/or minimum-temperature-value positions of a second quantity in the infrared human-body image.

In an embodiment of the present disclosure, the local extreme values in the infrared human-body image may be sorted. For example, the image positions where the first quantity of the local extreme values in the sorted sequence of the local extreme values in a descending order are used as the maximum-temperature-value positions, and the image positions where the first second quantity of the local extreme values in the sorted sequence of the local extreme values in an ascending order are used as the minimum-temperature-value positions. The ascending order or the descending order may be adjusted according to actual situations, which is merely illustratively described and not limited herein. The first quantity and the second quantity are the quantities of the minimum-temperature-value positions and the maximum-temperature-value positions, respectively, that are required to be selected, the first quantity and the second quantity are less than the total quantity of the Traditional-Chinese-Medicine human-body critical points in the infrared human-body image, and the first quantity and the second quantity may be equal or different. For example, both of the first quantity and the second quantity may be 3, or the first quantity may be 3 and the second quantity may be 2, which may be particularly configured according to practical demands, and is not limited herein.

Step 1032: determining the temperature type of the Traditional-Chinese-Medicine human-body critical point that corresponds to an image region where the maximum-temperature-value positions are located as the high-temperature type, and/or determining the temperature type of the Traditional-Chinese-Medicine human-body critical point that corresponds to an image region where the minimum-temperature-value positions are located as the low-temperature type.

In an embodiment of the present disclosure, because in the academic theory of the Traditional Chinese Medicine the Traditional-Chinese-Medicine body constitution is usually determined according to several body sites that have the highest temperatures and the lowest temperatures, by summarizing the minimum temperature values and the maximum temperature values in the infrared human-body image and then sorting them according to the magnitudes, the positions where the coldness and the hotness exhibit obviously can be identified out.

Figure 6:
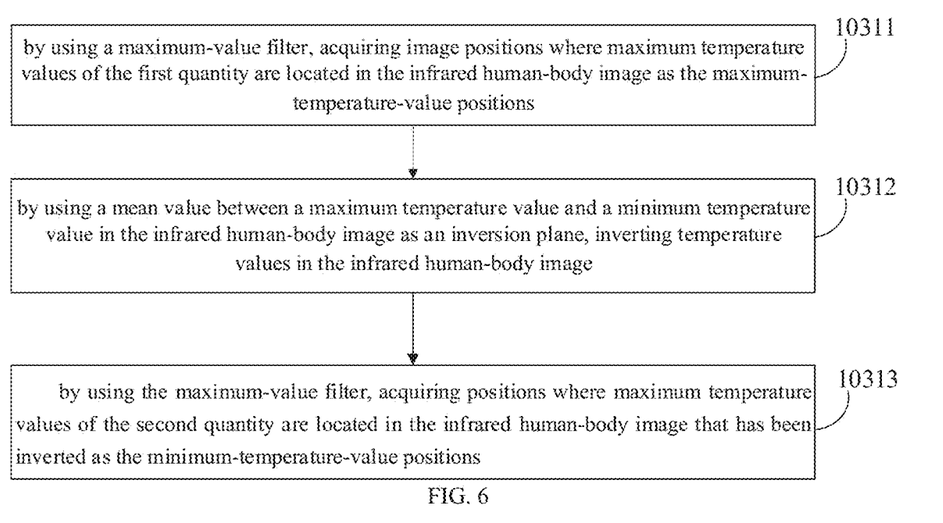
FIG. 6 schematically shows a third schematic flow chart of the method for identifying a body constitution in Traditional Chinese Medicine according to some embodiments of the present disclosure.

Optionally, referring to FIG. 6, the step 1031 may include:

Step 10311: by using a maximum-value filter, acquiring image positions where maximum temperature values of the first quantity are located in the infrared human-body image as the maximum-temperature-value positions.

In some embodiments of the present disclosure, a maximum-value filter may be a Peak_local_max local-maximum-value algorithm in a Skimage dataset in Opencv. Certainly, another filter having the maximum-value screening process may also be used to extract the maximum temperature values of the local image regions where the Traditional-Chinese-Medicine human-body critical points are located. For example, the step length of the algorithm is set to be 10.

Figure 7:
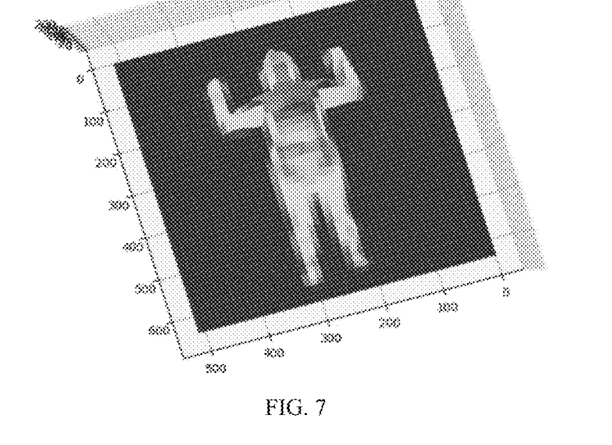
FIG. 7 schematically shows a schematic effect picture of the human-body infrared image according to some embodiments of the present disclosure.
Figure 8:
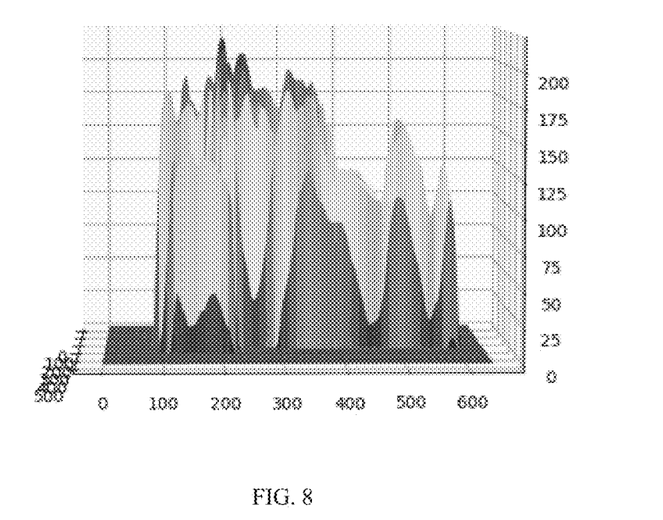
FIG. 8 schematically shows a schematic effect picture of another human-body infrared image according to some embodiments of the present disclosure.

FIG. 7 is a front view obtained by performing color dialysis to the human-body infrared image, wherein the temperatures are characterized by using different colors. Moreover, referring to FIG. 8, FIG. 8 is a side temperature chart of the human-body infrared image obtained by processing FIG. 7 by using the Peak_local_max local-maximum-value algorithm, wherein the vertical coordinate is the pixel value of the infrared image; in other words, if the temperature value is higher, the temperature is higher. Because infrared images have the characteristic of unclear boundary textures, the obtained front view cannot accurately characterize the profile of coldness and hotness of a human body. Moreover, regarding the side view obtained by processing by using the Peak_local_max local-maximum-value algorithm, merely the values of the pixel points in the human-body infrared image are required to be taken into consideration, which prevents the affection by the unclear boundary texture of the infrared image on the accuracy of the identification on the maximum-temperature-value positions and the minimum-temperature-value positions.

Step 10312: by using a mean value between a maximum temperature value and a minimum temperature value in the infrared human-body image as an inversion plane, inverting temperature values in the infrared human-body image.

In an embodiment of the present disclosure, because the method of assessing the coldness and hotness of human-body sites in the academic theory of the Traditional Chinese Medicine is based on the overall temperature-distribution profile of a human body, and, in order to ensure that the data space does not deviate, the mean value between the maximum temperature value and the minimum temperature value of the pixel values in the infrared human-body image may be used as the inversion plane to invert the temperature values of the infrared human-body image, thereby preventing the condition that deviation of the data space results in the emergence of a negative value among the temperature values after the inversion. For example, if the maximum temperature value is x and the minimum temperature value is y, then the inversion plane is $(x+y)/2$, in which case, for any temperature n in the infrared human-body image, the temperature that has been inverted is $(x+y)/2*2-n$.

Step 10313: by using the maximum-value filter, acquiring positions where maximum temperature values of the second quantity are located in the infrared human-body image that has been inverted as the minimum-temperature-value positions.

In an embodiment of the present disclosure, because the magnitudes of the temperature values in the infrared human-body image after the inversion are reverse, the maximum values may be re-extracted by using a maximum-value filter, and the maximum values can characterize the minimum temperature values in the infrared human-body image.

Optionally, the step 104 may include: in a Traditional-Chinese-Medicine-body-constitution mapping relation, inquiring Traditional-Chinese-Medicine body constitutions that match with temperature types of the Traditional-Chinese-Medicine human-body critical points.

In an embodiment of the present disclosure, a Traditional-Chinese-Medicine-body-constitution mapping relation may be provided by referring to the academic theory of the Traditional Chinese Medicine, wherein the Traditional-Chinese-Medicine-body-constitution mapping relation includes the Traditional-Chinese-Medicine body constitutions that correspond to the cases that the Traditional-Chinese-Medicine human-body critical points are of various temperature types, thereby conveniently identifying the Traditional-Chinese-Medicine body constitution of the target user.

Figure 9:
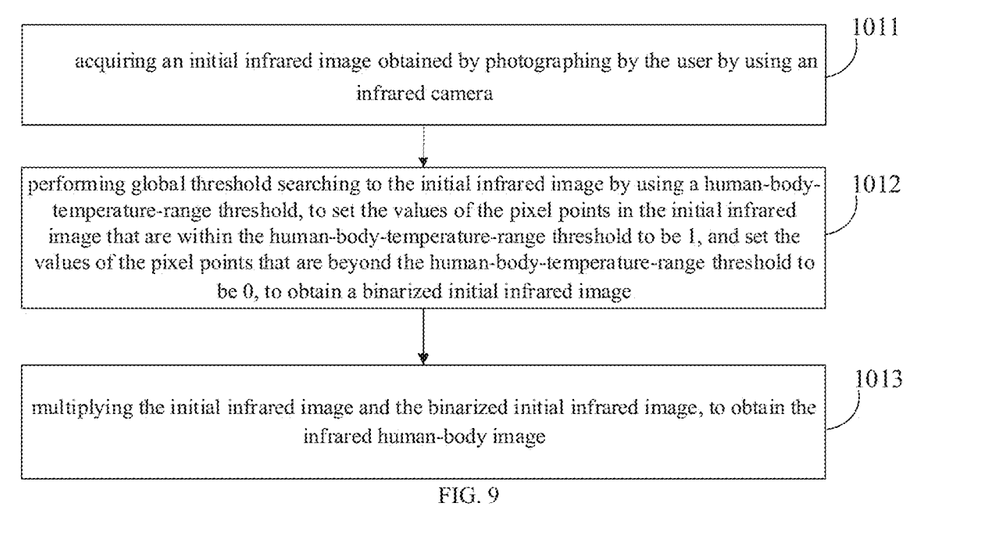
FIG. 9 schematically shows a fourth schematic flow chart of the method for identifying a body constitution in Traditional Chinese Medicine according to some embodiments of the present disclosure.

Optionally, referring to FIG. 9, the step 101 may include:

Step 1011: acquiring an initial infrared image obtained by photographing by the user by using an infrared camera.

In an embodiment of the present disclosure, because the scenes for collecting medical infrared images are not diverse, and users usually perform the infrared photographing in a dedicated photographing space of a hospital, irrelevant artificial interference is rare. However, there are still some irrelevant background-interference contents, and it is required to perform a background removing operation at the photographed initial infrared image.

Step 1012: performing global threshold searching to the initial infrared image by using a human-body-temperature-range threshold, to set the values of the pixel points in the initial infrared image that are within the human-bodytemperature-range threshold to be 1, and set the values of the pixel points that are beyond the human-body-temperature-range threshold to be 0, to obtain a binarized initial infrared image.

Figure 10:
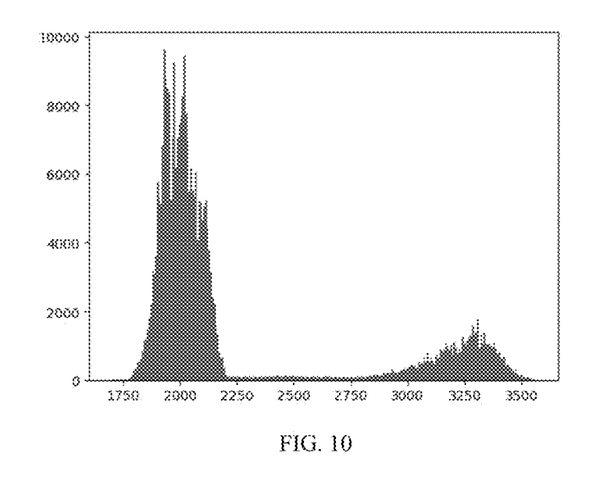
FIG. 10 schematically shows a schematic diagram of the principle of the method for identifying a body constitution in Traditional Chinese Medicine according to some embodiments of the present disclosure.

In an embodiment of the present disclosure, binarization processing is performed to the initial infrared image by using the human-body-temperature-range threshold. As an example, referring to FIG. 10, the histogram of the initial infrared image exhibits an obvious "double peak", and global threshold searching may be performed by using OTSU (the Otsu algorithm). Finally, threshold division is performed by using the obtained threshold, to obtain a mask image in which the values of the maintained pixel points of the human-body image region are 1 and the values of the pixel points of the background image region are 0. By multiplying the mask image and the initial infrared image, the infrared human-body image whose background has been removed can be obtained.

Step 1013: multiplying the initial infrared image and the binarized initial infrared image, to obtain the infrared human-body image.

The embodiments of the present disclosure, by performing binarization processing to the initial infrared image, and subsequently removing the irrelevant background image region in the initial infrared image, reduces the interference by irrelevant image contents on the subsequent identification on the Traditional-Chinese-Medicine human-body critical points, and improves the accuracy of the identification on the Traditional-Chinese-Medicine human-body critical points.

Figure 11:
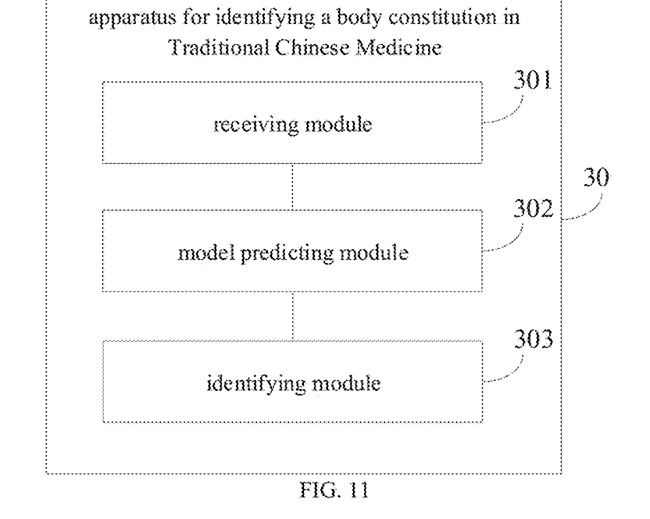
FIG. 11 schematically shows a schematic structural diagram of the apparatus for identifying a body constitution in Traditional Chinese Medicine according to some embodiments of the present disclosure.

FIG. 11 schematically shows a schematic structural diagram of the apparatus for identifying a body constitution in Traditional Chinese Medicine 30 according to the present disclosure. The apparatus includes:
  a receiving module 301 configured for acquiring an infrared human-body image of a target user;
  a model predicting module 302 configured for inputting the infrared human-body image into an infrared critical-point identifying model, to obtain a Traditional-Chinese-Medicine human-body critical point in the infrared human-body image; and
  an identifying module 303 configured for, according to a temperature-distribution profile in the infrared human-body image, determining a temperature type of the Traditional-Chinese-Medicine human-body critical point in the infrared human-body image; and
  according to the temperature type, identifying a Traditional-Chinese-Medicine body constitution of the target user.

Optionally, the apparatus further includes: a training module configured for:
  acquiring a natural-light critical-point identifying model and a sample infrared human-body image;
  marking the Traditional-Chinese-Medicine human-body critical point in the sample infrared human-body image; and
  performing transfer learning of the natural-light critical-point identifying model by using the sample infrared human-body image that has been marked, to obtain the infrared critical-point identifying model.

Optionally, the training module is further configured for:
  based on the Traditional-Chinese-Medicine human-body critical point, adjusting fully-connected-layer nodes of the natural-light critical-point identifying model; and
  while a model parameter of a feature-extraction layer is maintained unchanged, by using the sample infrared human-body image that has been marked, training the natural-light critical-point identifying model whose nodes have been adjusted, to obtain the infrared critical-point identifying model.

Optionally, original human-body critical points of the natural-light critical-point identifying model include the Traditional-Chinese-Medicine human-body critical point, and a quantity of the original human-body critical points is greater than a quantity of the Traditional-Chinese-Medicine human-body critical point; and
  optionally, the training module is further configured for:
  among the fully-connected-layer nodes of the natural-light critical-point identifying model, deleting a fully-connected-layer node whose node label corresponds to a human-body critical point that is not the Traditional-Chinese-Medicine human-body critical point.

Optionally, a feature-extraction network in the natural-light critical-point identifying model is a lightweight feature-extraction network, wherein a parameter data volume of the lightweight feature-extraction network is less than a parameter data volume of an original feature-extraction network of the natural-light critical-point identifying model.

Optionally, the temperature type includes at least one of a high-temperature type and a low-temperature type; and
  the identifying module 303 is further configured for:
  determining maximum-temperature-value positions of a first quantity and/or minimum-temperature-value positions of a second quantity in the infrared human-body image; and
  determining the temperature type of the Traditional-Chinese-Medicine human-body critical point that corresponds to an image region where the maximum-temperature-value positions are located as the high-temperature type, and/or determining the temperature type of the Traditional-Chinese-Medicine human-body critical point that corresponds to an image region where the minimum-temperature-value positions are located as the low-temperature type.

Optionally, the identifying module 303 is further configured for:
  by using a maximum-value filter, acquiring image positions where maximum temperature values of the first quantity are located in the infrared human-body image as the maximum-temperature-value positions;
  by using a mean value between a maximum temperature value and a minimum temperature value in the infrared human-body image as an inversion plane, inverting temperature values in the infrared human-body image; and
  by using the maximum-value filter, acquiring positions where maximum temperature values of the second quantity are located in the infrared human-body image that has been inverted as the minimum-temperature-value positions.

Optionally, the identifying module 303 is further configured for:
  in a Traditional-Chinese-Medicine-body-constitution mapping relation, inquiring Traditional-Chinese-Medicine body constitutions that match with temperature types of the Traditional-Chinese-Medicine human-body critical points.

Optionally, the receiving module 301 is further configured for:
  acquiring an initial infrared image obtained by photographing by the user by using an infrared camera;
  performing global threshold searching to the initial infrared image by using a human-body-temperature-range threshold, to set the values of the pixel points in the initial infrared image that are within the human-bodytemperature-range threshold to be 1, and set the values of the pixel points that are beyond the human-body-temperature-range threshold to be 0, to obtain a binarized initial infrared image; and multiplying the initial infrared image and the binarized initial infrared image, to obtain the infrared human-body image.

Optionally, the training module is further configured for:

based on the Traditional-Chinese-Medicine human-body critical point, adjusting fully-connected-layer nodes of the natural-light critical-point identifying model; and while some of the predetermined model parameters of a feature-extraction layer are maintained unchanged, by using the sample infrared human-body image that has been marked, training the natural-light critical-point identifying model whose nodes have been adjusted, to obtain the infrared critical-point identifying model.

Optionally, the Traditional-Chinese-Medicine human-body critical point includes at least one of a head critical point, a neck critical point, a shoulder critical point, an elbow critical point, a hand critical point, an abdomen critical point, a crotch critical point, a knee critical point and a foot critical point.

In the embodiments of the present disclosure, the temperature types of the sites of the body of the user are identified by using the infrared critical-point identifying model to determine the Traditional-Chinese-Medicine body constitution of the user, which prevents errors in the distinguishing of the temperature types caused by artificial negligence, and improves the accuracy of the identification on the Traditional-Chinese-Medicine body constitution.

The above-described device embodiments are merely illustrative, wherein the units that are described as separate components may or may not be physically separate, and the components that are displayed as units may or may not be physical units; in other words, they may be located at the same one location, and may also be distributed to a plurality of network units. Some or all of the modules may be selected according to the actual demands to realize the purposes of the solutions of the embodiments. A person skilled in the art can understand and implement the technical solutions without paying creative work.

Each component embodiment of the present disclosure may be implemented by hardware, or by software modules that are operated on one or more processors, or by a combination thereof. A person skilled in the art should understand that some or all of the functions of some or all of the components of the computing and processing device according to the embodiments of the present disclosure may be implemented by using a microprocessor or a digital signal processor (DSP) in practice. The present disclosure may also be implemented as apparatus or device programs (for example, computer programs and computer program products) for implementing part of or the whole of the method described herein. Such programs for implementing the present disclosure may be stored in a computer-readable medium, or may be in the form of one or more signals. Such signals may be downloaded from an Internet website, or provided on a carrier signal, or provided in any other forms.

Figure 12:
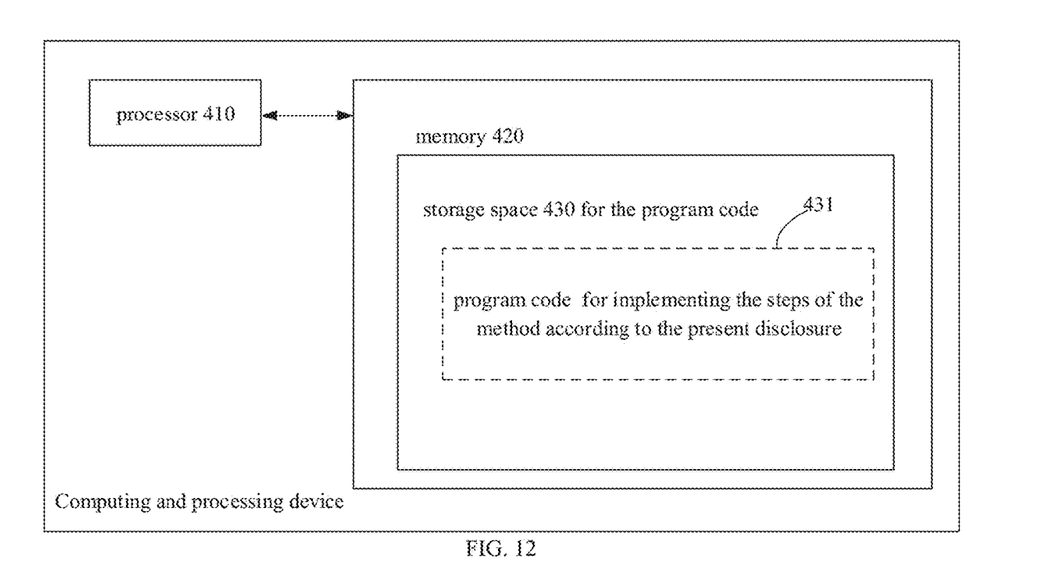
FIG. 12 schematically shows a block diagram of a computing and processing device for executing the method according to some embodiments of the present disclosure.
Figure 13:
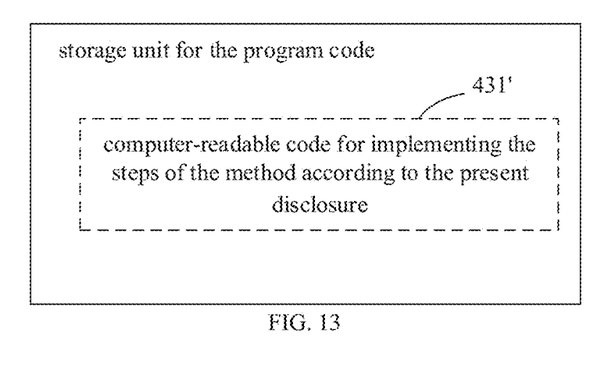
FIG. 13 schematically shows a storage unit for maintaining or carrying a program code for executing the method according to some embodiments of the present disclosure.

For example, FIG. 12 shows a computing and processing device that can implement the method according to the present disclosure. The computing and processing device traditionally include a processor 410 and a computer program product or computer-readable medium in the form of a memory 420. The memory 420 may be electronic memories such as flash memory, EEPROM (Electrically Erasable Programmable Read Only Memory), EPROM, hard disk or ROM. The memory 420 has the storage space 430 of the program code 431 for implementing any steps of the above method. For example, the storage space 430 for program code may contain program codes 431 for individually implementing each of the steps of the above method. Those program codes may be read from one or more computer program products or be written into the one or more computer program products. Those computer program products include program code carriers such as a hard disk, a compact disk (CD), a memory card or a floppy disk. Such computer program products are usually portable or fixed storage units as shown in FIG. 13. The storage unit may have storage segments or storage spaces with similar arrangement to the memory 420 of the computing and processing device in FIG. 12. The program codes may, for example, be compressed in a suitable form. Generally, the storage unit contains a computer-readable code 431', which can be read by a processor like 410. When those codes are executed by the computing and processing device, the codes cause the computing and processing device to implement each of the steps of the method described above.

It should be understood that, although the steps in the flow charts in the drawings are shown sequentially according to the indication by the arrows, those steps are not necessarily performed sequentially according to the sequence indicated by the arrows. Unless expressly described herein, the sequence of the performances of those steps are not strictly limited, and they may be performed in other sequences. Furthermore, at least some of the steps in the flow charts in the drawings may include a plurality of sub-steps or a plurality of stages, wherein those sub-steps or stages are not necessarily completely performed at the same one moment, but may be performed at different moments, and their performance sequence is not necessarily sequential performance, but may be performance alternate with at least some of the other steps or the sub-steps or stages of the other steps.

The "one embodiment", "an embodiment" or "one or more embodiments" as used herein means that particular features, structures or characteristics described with reference to an embodiment are included in at least one embodiment of the present disclosure. Moreover, it should be noted that here an example using the wording "in an embodiment" does not necessarily refer to the same one embodiment.

The description provided herein describes many concrete details. However, it can be understood that the embodiments of the present disclosure may be implemented without those concrete details. In some of the embodiments, well-known processes, structures and techniques are not described in detail, so as not to affect the understanding of the description.

In the claims, any reference signs between parentheses should not be construed as limiting the claims. The word "include" does not exclude elements or steps that are not listed in the claims. The word "a" or "an" preceding an element does not exclude the existing of a plurality of such elements. The present disclosure may be implemented by means of hardware including several different elements and by means of a properly programmed computer. In unit claims that list several devices, some of those devices may be embodied by the same item of hardware. The words first, second, third and so on do not denote any order. Those words may be interpreted as names.

Finally, it should be noted that the above embodiments are merely intended to explain the technical solutions of the present disclosure, and not to limit them. Although the present disclosure is explained in detail with reference to the above embodiments, a person skilled in the art should understand that he can still modify the technical solutions set forth by the above embodiments, or make equivalent substitutions to part of the technical features of them. However, those modifications or substitutions do not make the essence of the corresponding technical solutions depart from the spirit and scope of the technical solutions of the embodiments of the present disclosure.

The invention claimed is:

1. A method for identifying a body constitution in Traditional Chinese Medicine, wherein the method comprises:
   acquiring an infrared human-body image of a target user;
   inputting the infrared human-body image into an infrared critical-point identifying model, to obtain a Traditional-Chinese-Medicine human-body critical point in the infrared human-body image;
   according to a temperature-distribution profile in the infrared human-body image, determining a temperature type of the Traditional-Chinese-Medicine human-body critical point in the infrared human-body image; and
   according to the temperature type, identifying a Traditional-Chinese-Medicine body constitution of the target user,
   wherein the temperature type comprises at least one of a high-temperature types and a low-temperature type; and
   the step of, according to the temperature-distribution profile in the infrared human-body image, determining the temperature type of the Traditional-Chinese-Medicine human-body critical point in the infrared human-body image comprises:
   determining maximum-temperature-value positions of a first quantity and/or minimum-temperature-value positions of a second quantity in the infrared human-body image; and
   determining the temperature type of the Traditional-Chinese-Medicine human-body critical point that corresponds to an image region where the maximum-temperature-value positions are located as the high-temperature type, and/or determining the temperature type of the Traditional-Chinese-Medicine human-body critical point that corresponds to an image region where the minimum-temperature-value positions are located as the low-temperature type; and
   wherein the step of determining the maximum-temperature-value positions of the first quantity and/or the minimum-temperature-value positions of the second quantity in the infrared human-body image comprises:
   by using a maximum-value filter, acquiring image positions where maximum temperature values of the first quantity are located in the infrared human-body image as the maximum-temperature-value positions;
   by using a mean value between a maximum temperature value and a minimum temperature value in the infrared human-body image as an inversion plane, inverting temperature values in the infrared human-body image; and
   by using the maximum-value filter, acquiring positions where maximum temperature values of the second quantity are located in the infrared human-body image that has been inverted as the minimum-temperature-value positions.

2. The method according to claim 1, wherein the infrared critical-point identifying model is obtained by the following steps:
   acquiring a natural-light critical-point identifying model and a sample infrared human-body image;
   marking the Traditional-Chinese-Medicine human-body critical point in the sample infrared human-body image; and
   performing transfer learning of the natural-light critical-point identifying model by using the sample infrared human-body image that has been marked, to obtain the infrared critical-point identifying model.

3. The method according to claim 2, wherein the step of performing transfer learning of the natural-light critical-point identifying model by using the sample infrared human-body image that has been marked, to obtain the infrared critical-point identifying model comprises:
   based on the Traditional-Chinese-Medicine human-body critical point, adjusting fully-connected-layer nodes of the natural-light critical-point identifying model; and
   while a model parameter of a feature-extraction layer is maintained unchanged, by using the sample infrared human-body image that has been marked, training the natural-light critical-point identifying model whose nodes have been adjusted, to obtain the infrared critical-point identifying model.

4. The method according to claim 3, wherein original human-body critical points of the natural-light critical-point identifying model comprise the Traditional-Chinese-Medicine human-body critical point, and a quantity of the original human-body critical points is greater than a quantity of the Traditional-Chinese-Medicine human-body critical point; and
   the step of, based on the Traditional-Chinese-Medicine human-body critical point, adjusting the fully-connected-layer nodes of the natural-light critical-point identifying model comprises:
   among the fully-connected-layer nodes of the natural-light critical-point identifying model, deleting a fully-connected-layer node whose node label corresponds to a human-body critical point that is not the Traditional-Chinese-Medicine human-body critical point.

5. The method according to claim 3, wherein the step of, according to the temperature type, identifying the Traditional-Chinese-Medicine body constitution of the target user comprises:
   in a Traditional-Chinese-Medicine-body-constitution mapping relation, inquiring Traditional-Chinese-Medicine body constitutions that match with temperature types of the Traditional-Chinese-Medicine human-body critical points.

6. The method according to claim 4, wherein the step of, according to the temperature type, identifying the Traditional-Chinese-Medicine body constitution of the target user comprises:
   in a Traditional-Chinese-Medicine-body-constitution mapping relation, inquiring Traditional-Chinese-Medicine body constitutions that match with temperature types of the Traditional-Chinese-Medicine human-body critical points.

7. The method according to claim 2, wherein the step of performing transfer learning of the natural-light critical-point identifying model by using the sample infrared human-body image that has been marked, to obtain the infrared critical-point identifying model comprises:
   based on the Traditional-Chinese-Medicine human-body critical point, adjusting fully-connected-layer nodes of the natural-light critical-point identifying model; and
   by using the sample infrared human-body image that has been marked, training the natural-light critical-point identifying model whose nodes have been adjusted, to obtain the infrared critical-point identifying model.

8. The method according to claim 7, wherein the step of, according to the temperature type, identifying the Traditional-Chinese-Medicine body constitution of the target user comprises:
- in a Traditional-Chinese-Medicine-body-constitution mapping relation, inquiring Traditional-Chinese-Medicine body constitutions that match with temperature types of the Traditional-Chinese-Medicine human-body critical points.

9. The method according to claim 2, wherein a feature-extraction network in the natural-light critical-point identifying model is a lightweight feature-extraction network, wherein a parameter data volume of the lightweight feature-extraction network is less than a parameter data volume of an original feature-extraction network of the natural-light critical-point identifying model.

10. The method according to claim 9, wherein the step of, according to the temperature type, identifying the Traditional-Chinese-Medicine body constitution of the target user comprises:
- in a Traditional-Chinese-Medicine-body-constitution mapping relation, inquiring Traditional-Chinese-Medicine body constitutions that match with temperature types of the Traditional-Chinese-Medicine human-body critical points.

11. The method according to claim 2, wherein the Traditional-Chinese-Medicine human-body critical point comprises at least one of a head critical point, a neck critical point, a shoulder critical point, an elbow critical point, a hand critical point, an abdomen critical point, a crotch critical point, a knee critical point and a foot critical point.

12. The method according to claim 11, wherein the step of, according to the temperature type, identifying the Traditional-Chinese-Medicine body constitution of the target user comprises:
- in a Traditional-Chinese-Medicine-body-constitution mapping relation, inquiring Traditional-Chinese-Medicine body constitutions that match with temperature types of the Traditional-Chinese-Medicine human-body critical points.

13. The method according to claim 2, wherein the step of, according to the temperature type, identifying the Traditional-Chinese-Medicine body constitution of the target user comprises:
- in a Traditional-Chinese-Medicine-body-constitution mapping relation, inquiring Traditional-Chinese-Medicine body constitutions that match with temperature types of the Traditional-Chinese-Medicine human-body critical points.

14. The method according to claim 1, wherein the step of, according to the temperature type, identifying the Traditional-Chinese-Medicine body constitution of the target user comprises:
- in a Traditional-Chinese-Medicine-body-constitution mapping relation, inquiring Traditional-Chinese-Medicine body constitutions that match with temperature types of the Traditional-Chinese-Medicine human-body critical points.

15. A computing and processing device, wherein the computing and processing device comprises:
- a memory storing a computer-readable code; and
- one or more processors, wherein when the computer-readable code is executed by the one or more processors, the computing and processing device executes the method for identifying a body constitution in Traditional Chinese Medicine according to claim 1.

16. A non-transitory computer-readable medium, wherein the computer-readable medium stores a computer program of the method for identifying a body constitution in Traditional Chinese Medicine according to claim 1.

* * * * *